(12) United States Patent
Farmer et al.

(10) Patent No.: US 11,653,656 B2
(45) Date of Patent: *May 23, 2023

(54) BAKED GOODS

(71) Applicant: Ganeden Biotech, Inc., Mayfield Heights, OH (US)

(72) Inventors: Sean Farmer, Miami Beach, FL (US); Andrew R. Lefkowitz, Mayfield Heights, OH (US); Michael A. Bush, Cleveland, OH (US); David T. Maske, Chagrin Falls, OH (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/543,491

(22) Filed: Aug. 16, 2019

(65) Prior Publication Data

US 2020/0000106 A1 Jan. 2, 2020

Related U.S. Application Data

(63) Continuation of application No. 12/229,862, filed on Aug. 27, 2008, now Pat. No. 10,383,342.

(60) Provisional application No. 60/966,897, filed on Aug. 29, 2007.

(51) Int. Cl.
| | |
|---|---|
| *A21D 8/04* | (2006.01) |
| *A23L 7/104* | (2016.01) |
| *A23L 19/18* | (2016.01) |
| *A23P 10/30* | (2016.01) |
| *A23L 7/13* | (2016.01) |
| *A23L 33/135* | (2016.01) |
| *C12N 1/20* | (2006.01) |
| *C12R 1/07* | (2006.01) |

(52) U.S. Cl.
CPC .............. *A21D 8/045* (2013.01); *A21D 8/04* (2013.01); *A23L 7/104* (2016.08); *A23L 7/13* (2016.08); *A23L 19/18* (2016.08); *A23L 33/135* (2016.08); *A23P 10/30* (2016.08); *C12N 1/205* (2021.05); *A23V 2002/00* (2013.01); *C12R 2001/07* (2021.05)

(58) Field of Classification Search
CPC .......... A21D 8/045; A21D 8/04; A23L 7/104; A23L 33/135; A23L 19/18; A23L 7/13; A23L 33/105; C12R 1/07; A23P 10/30; C12N 1/205
USPC .......................................................... 426/61
See application file for complete search history.

(56) References Cited

U.S. PATENT DOCUMENTS

| | | | | |
|---|---|---|---|---|
| 5,968,569 | A * | 10/1999 | Cavadini | A61K 35/742 426/61 |
| 6,835,397 | B2 * | 12/2004 | Lee | A21D 8/047 424/461 |
| 2005/0100535 | A1 * | 5/2005 | Farmer | A23L 33/135 424/93.46 |

OTHER PUBLICATIONS

JP-10-084-845—Machine Translation (Year: 1998).*
Majeed, M. et al. Int. J. Food Sci. Technol. 51-894-901 (Year: 2016).*

* cited by examiner

*Primary Examiner* — Hamid R Badr
(74) *Attorney, Agent, or Firm* — Sughrue Mion, PLLC

(57) ABSTRACT

The present invention describes compositions and methods comprising lactic acid-producing bacteria in baked goods.

21 Claims, No Drawings

BAKED GOODS

RELATED APPLICATIONS

This application is a continuation of U.S. application Ser. No. 12/229,862, filed Aug. 27, 2008, which claims the benefit of U.S. Ser. No. 60/966,897, filed Aug. 29, 2007, which are incorporated herein by reference in their entirety.

FIELD OF THE INVENTION

The present invention relates to the use of lactic acid-producing bacteria in baked goods.

BACKGROUND

The gastrointestinal microflora plays a number of vital roles in maintaining gastrointestinal tract function and overall physiological health. The growth and metabolism of the many individual bacterial species inhabiting the gastrointestinal tract depend primarily upon the substrates available to them, most of which are derived from the diet. (See e.g., Gibson G. R. et al., 1995. *Gastroenterology* 106: 975-982; Christl, S. U. et al., 1992. *Gut* 33: 1234-1238). These findings have led to attempts to modify the composition and metabolic activities of the bacterial community through diet, primarily with probiotics, which are live microbial food supplements.

Probiotic organisms are non-pathogenic, non-toxigenic, retain viability during storage, and survive passage through the stomach and small intestine. Since probiotics do not generally permanently colonize the host, they need to be ingested regularly for any health promoting properties to persist.

SUMMARY OF THE INVENTION

The invention describes the use of acid-producing bacteria in baked goods for human or animal consumption. Specifically, the invention provides compositions comprising a baked composition of an edible starch and an isolated *Bacillus coagulans* bacterium and methods of administering probiotic bacterial spores to a human or other animal by providing a baked good containing the spores to the human or other animal whereby the human or animal ingests the baked good and the spores germinate in the gastrointestinal tract (stomach or small intestine). Germination of spores and/or colonization of gastrointestinal tissue by the administered bacterial spores or cells is assessed by detecting the probiotic microorganism in the stool of the individual.

An exemplary baked good includes a bread, a cake, a pie, a tart, a pastry, a candy bar, an energy bar, a food bar, granola, a granola bar, a quiche, a cookie, cereal, a pizza, a corn chip, a tortilla chip, a potato chip, a baked cracker, a dehydrated vegetable, a dehydrated fruit, or a treat for companion animals. In another aspect, the baked good includes any good comprising flour. In yet another aspect, the baked good of the invention includes any good that is heated, e.g., baked (exposure of dry heat). Preferably, the baked good is a muffin. In one aspect, the baked good is a blueberry bran muffin.

Optionally, the baked composition also includes a fat. Suitable fats include oils, butters, shortenings, artificial lipids, synthetic fats, and a fat substitutes. In another aspect, the baked composition also includes a sugar, sugar substitute, or artificial sweetener.

In one aspect, the isolated *Bacillus coagulans* comprise between about 0.01% to about 50% by weight of the baked good. Optionally, the isolated *Bacillus coagulans* comprise between about 0.01% and about 10% by weight of the baked good. Preferably, the isolated *Bacillus coagulons* comprise between about 0.01% and about 0.1% by weight of the baked good.

The invention also provides bacterial species including *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30, ATCC Designation Number PTA-6086; and CGI-40, ATCC Designation Number PTA-6087; see U.S. Pat. No. 6,849,256 to Farmer).

Optionally, the isolated *Bacillus coagulans* is in the form of a spore. Alternatively, the isolated *Bacillus coagulans* is in the form of a vegetative cell. In another aspect, the isolated *Bacillus coagulans* is in the form of a mixture of vegetative cells and spores.

The invention also provides for methods of making a baked good, wherein the baked good comprises a flour containing base mix and a liquid portion of water. Optionally, the method includes providing a flour containing base mix and a liquid portion of water; mixing the flour containing base mix and water to form a batter or dough; applying an isolated *Bacillus coagulans* bacterium to the batter or dough, and heat processing the batter or dough to cook the baked good. Alternatively, the method includes providing a flour containing base mix and a liquid portion of water; mixing the flour containing base mix and water to form a batter or dough; combining an isolated *Bacillus coagulans* bacterium with the batter or dough, and heat processing the batter or dough to cook the baked good.

Optionally, the isolated *Bacillus coagulans* is *Bacillus coagulans* hammer strain Accession No. ATCC 31284. In an exemplary embodiment, the isolated *Bacillus coagulans* is GBI-30 strain (ATCC Designation Number PTA-6086). In one aspect, the isolated *Bacillus coagulans* is in the form of a spore. Alternatively, the isolated *Bacillus coagulans* is in the form of a vegetative cell. In a preferred embodiment, the isolated *Bacillus coagulans* comprise between 1% and 10% by weight of the baked good.

The invention also provides compositions comprising a dry mix for baked goods including a flour and an isolated *Bacillus coagulans* bacterium.

The *Bacillus coagulans* Hammer strains of the invention are non-pathogenic and generally regarded as safe for use in human nutrition (i.e., GRAS classification) by the U.S. Federal Drug Administration (FDA) and the U.S. Department of Agriculture (USDA), and by those skilled in the art. Furthermore, the *Bacillus coagulans* Hammer strains of the invention germinate at or below human body temperature, rendering them useful as probiotics. Many *Bacillus coagulans* strains outside the Hammer group have mostly industrial applications, little or no nutritional benefit, and environmental contaminants that have not been evaluated for safety. Moreover, many other non-Hammer strains of *Bacillus coagulans* grow optimally at temperatures that exceed human body temperature and, thus, do not germinate efficiently in the human body. Such strains are less or not suitable as probiotics for human consumption.

Cited publications are incorporated herein by reference. Both the foregoing general description and the following detailed description and examples are exemplary and explanatory only and are not restrictive of the invention as claimed.

DETAILED DESCRIPTION

The present invention is directed to the discovery that non-pathogenic lactic acid-producing bacteria (i.e., "lactic acid bacteria"), such as the exemplary *Bacillus coagulans*, are useful in baked compositions as a probiotic.

Probiotic Lactic Acid-Producing Bacteria

A probiotic lactic acid-producing bacteria suitable for use in the methods and compositions of the invention produces acid and is non-pathogenic. There are many suitable bacteria identified as described herein, although the invention is not limited to currently known bacterial species insofar as the purposes and objectives of the bacteria is described. The property of acid production is important to the effectiveness of the probiotic lactic acid-producing bacteria of this invention.

The invention provides using a lactic acid-producing bacteria, such as a spore-forming *Bacillus* species, such as *B. coagulans*. Preferably, the spore-forming *Bacillus* species of the invention is *B. coagulans* Hammer.

Exemplary methods and compositions are described herein using *Bacillus coagulans* as a probiotic. Purified and/or isolated *Bacillus coagulans* is particularly useful as a probiotic in baked edible food products. Probiotic *B. coagulans* is non-pathogenic and is generally regarded as safe (i.e., GRAS classification) by the U.S. Federal Drug Administration (FDA) and the U.S. Department of Agriculture (USDA), and by those skilled in the art.

*Bacillus coagulans* is a non-pathogenic gram positive spore-forming bacteria that produces L(+) lactic acid (dextrorotatory) in fermentation conditions. It has been isolated from natural sources, such as heat-treated soil samples inoculated into nutrient medium (Bergey's Manual off Systemic Bacteriology, Vol. 2, Sneath, P. H. A. et al., eds., Williams & Wilkins, Baltimore, Md., 1986). Purified *B. coagulans* strains have served as a source of enzymes including endonucleases (e.g., U.S. Pat. No. 5,200,336); amylase (U.S. Pat. No. 4,980,180); lactase (U.S. Pat. No. 4,323,651); and cyclo-malto-dextrin glucano-transferase (U.S. Pat. No. 5,102,800). *B. coagulans* has been used to produce lactic acid (U.S. Pat. No. 5,079,164). A strain of *B. coagulans* (referred to as *L. sporogenes*; Sakaguti & Nakayama (ATCC 31284)) has been combined with other lactic acid producing bacteria and *B. natto* to produce a fermented food product from steamed soybeans (U.S. Pat. No. 4,110,477).

Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30, ATCC Designation Number PTA-6086; and GBI-40, ATCC Designation Number PTA-6087; see U.S. Pat. No. 6,849,256 to Farmer).

*Bacillus coagulans* was previously mis-characterized as a *Lactobacillus* and labeled as *Lactobacillus sporogenes* (See Nakamura et al. 1988. *Int. J. Syst. Bacteriol.* 38: 63-73). However, initial classification was incorrect because *Bacillus coagulans* produces spores and excretes L(+)-lactic acid through metabolism. Both of these characteristics provide key features to the utility of *Bacillus coagulans*. These developmental and metabolic aspects required that the bacterium be classified as a lactic acid *Bacillus*. In addition, it is not generally appreciated that classic *Lactobacillus* species are unsuitable for colonization of the gut due to their instability in the harsh (i.e., acidic) pH environment of the bile, particularly human bile. By contrast, *Bacillus coagulans* is able to survive and colonize the gastrointestinal tract in the bile environment and even grown in this low pH range.

Probiotic Activity of *Bacillus coagulans*

It is well-documented clinically that many species of bacterial, mycotic and yeast pathogens possess the ability to cause a variety of gastrointestinal disorders including, but not limited to: disruption of normal gastrointestinal biochemical function, necrosis of gastrointestinal tissues, and disruption of the bioabsorption of nutrients, and like conditions. The probiotic microorganism-containing compositions of the present invention inhibit these pathogens. Thus, the compositions of the invention are useful in the prophylactic or therapeutic treatment of conditions associated with infection by these aforementioned pathogens.

In one aspect, a *Bacillus coagulans* strain is included in the composition in the form of vegetative cells. Alternatively, the *Bacillus coagulans* strain is included in the composition in the form of spores. The invention also provides for including the *Bacillus coagulans* strain in the composition in the form of a dried cell mass, a stabilized paste, or a stabilized gel.

Because *Bacillus* spores are heat and pressure-resistant and can be stored as a dry power, they are particularly useful for formulation into and manufacture of products such as the various baked products and compositions described herein. A *Bacillus* species is well suited for the present invention, particularly species having the ability to form spores which are relatively resistant to heat and other conditions, making them ideal for storage (shelf-life) in product formulations.

Tthe *Bacillus coagulans* of the invention survives storage (shelf-life) from about 12 days to about 2 years; from about 1 month to about 18 months; from about 3 months to about 1 year; or from about 6 months to about 9 months. For example, spores baked into a muffin remain viable and germination-competent for the self-life of the muffin (e.g., 6-12 days).

Micro-Encapsulation

In one aspect, the lactic-acid producing bacteria are incorporated into a microcapsule coating prior to addition to the baked good, using any micro-encapsulation process well-known in the art. The isolated *Bacillus coagulans* are packaged, or encapsulated, within another material in order to protect the bacteria from the surrounding environment. The capsules of the invention range in size from one-thousandth of a millimeter to seven millimeters. The internal ingredients of the microcapsule are released from their shells in various ways, including mechanical rupture of the capsule wall, dissolution of the wall, melting of the wall and diffusion through the wall. Thus, micro-encapsulation provides additional protection to the isolated *Bacillus* bacterium during heat processing (baking) of the baked goods of the invention. Physical methods of micro-encapsulation include pan coating, air-suspension coating, centrifugal extrusion, vibrational nozzle, and spray-drying. Chemical methods of micro-encapsulation include interfacial polymerization, in-situ polymerization, and matrix polymerization.

Alternatively, the lactic-acid producing bacteria is added to the baked good without micro-encapsulation.

Baked Goods

The invention is directed to the surprising discovery that lactic acid-producing bacteria, particularly *Bacillus* species, remain viable and retain their beneficial probiotic properties in heated/cooked baked goods, as the baked goods of the invention are heated to between about 300° F. to about 475° F. for about 5 minutes; about 10 minutes; about 30 minutes; or about 1 hour. In one aspect, the baked goods of the invention are heated up to about 350° F. for about 14 minutes; about 450° F. for about 17 minutes; or about 475° F. for about 6 minutes. The preferred heat and duration will vary depending upon the particular baked good. In one aspect, muffins are heated up to about 350° F. to about 375° F. for about 14 to about 20 minutes. In another aspect, cereal is heated up to about 475° F. for about 6 minutes.

As discussed further, the compositions are formulated in many configurations because the bacterium is present as a vegetative cell or as a spore, or both, depending on the species and form of the probiotic organism. The cells/spores are present in a variety of compositions suited for use in a baked good. In one aspect, the bacterium is present as a mixture of spores and vegetative cells. Preferably, the bacterium is present as at least 90% spores, e.g., 95%, 98%, or 99% spores.

An exemplary baked good includes a bread, a cake, a pie, a tart, a pastry, a candy bar, an energy bar, granola, a granola bar, a quiche, a cookie, cereal, a food bar, a pizza, a corn chip, a tortilla chip, a potato chip, a baked cracker, a dehydrated vegetable, or a treat for companion animals. In another aspect, the baked good includes any good comprising flour. In yet another aspect, the baked good of the invention includes any good that is heated. The invention provides for baked compositions baked/cooked in an oven. The compositions described herein are baked, or dried by subjecting them to heat. Alternatively, the baked compositions are steam-heated using high heat and excessive moisture, e.g., from about 10% to about 50% w/w water/dough prior to baking. Preferably, the baked composition comprises about 30-50% w/w water/dough; about 15-30% w/w water/dough; or about 5-15% w/w water/dough prior to baking. The invention also provides for confectionary compositions such as sweets, lollipops, candy bars, chocolate, and other sweet items of snack food.

Bread consists minimally of flour and water; salt is present in most cases, and usually a leavening agent such as yeast is used; however, any well-recognized method of making bread is used in the present invention. Optionally, the flour is wheat flour, rice four, corn flour, rye flour, potato flour, millet flour, baking flour, graham flour or quinoa flour. In one aspect, the flour is self-rising or self-raising flour. In some cases, bread also contains some amounts of sugar, spices, fruit (such as raisins, pumpkins, bananas, strawberries, blueberries, and the like), vegetables (such as onion or zucchini, and the like), nuts, or seeds (such as caraway, sesame or poppy seeds). Optionally, a fat such as an oil (vegetable oil, corn oil, olive oil, grape seed oil, nut oil or fruit oil), butter, shortening, artificial lipid, synthetic fat, or a fat substitute such as olestra is also present. In yet another aspect, a sugar, sugar substitute, or artificial sweetener such as saccharin, sucralose or aspartame is present. Suitable baked goods include, but are not limited to, buns, rolls, bagels, cookies, and pastries. Preferably, the baked good is a blueberry bran muffin.

The *Bacillus* bacterium is impregnated into the baked good during the manufacturing process of the baked good (e.g., added to the batter or dough mix). The pressure and heat resistance of *Bacillus* spores makes them particularly suitable for incorporation into the baked good prior to heat processing (baking) to cook the baked good.

In one aspect, the probiotic lactic acid-producing bacteria is introduced into or onto portions of the baked good by applying a composition containing viable bacteria to the baked good during a stage of the manufacture of the baked good. Preferably, the spores and/or vegetative cells of the probiotic acid-producing bacteria are introduced into batter or dough prior to baking the baked good. Alternatively, the bacteria is added during the baking process or after the baking process has concluded.

Preferably, the *Bacillus* bacterium is introduced into the batter prior to cooking the baked good. The invention provides a batter comprising a liquid mixture, usually based on one or more flours combined with liquids, such as water, milk or beer. In one aspect, egg is included in the batter. Optionally, a leavening agent is included in the mixture to aerate and fluff-up the batter as it cooks. In one embodiment, the viscosity of batter is very "stiff" (adhering to an upturned spoon). Alternatively, the viscosity of the batter is very "thin" (similar to single cream). Preferably, heat is applied to the batter by baking, in order to cook the ingredients (thus rendering them palatable) and to "set" the batter into a solid form. Following the baking process, the baked product is suitable for immediate human or animal consumption or for freezing, i.e., to store the product for future consumption.

The invention also provides for applying the *Bacillus* bacterium to a baked good using any of a variety of known methods including, for example, applying a powder, spray-drying the probiotic onto the baked good or soaking the baked good in a solution containing the probiotic. Optionally, the *Bacillus* bacterium is applied prior to cooking the baked good. Alternatively, the *Bacillus* bacterium is applied during or after the baking process has been completed.

The invention provides for a variety of methods for placing the bacterial composition onto a baked good. However, preferred methods include a "spray-dry" method in which the baked good is exposed in a low humidity chamber to an atomized mix containing a liquid composition, where the chamber is subsequently exposed to approximately 80-110° F. to dry the liquid, thereby impregnating the material of the baked good with the components of the composition.

A typical concentration is from approximately $1 \times 10^7$ to $1 \times 10^{12}$ CFU; $1 \times 10^8$ to $1 \times 10^{11}$ CFU; or $1 \times 10^9$ to $1 \times 10^{10}$ CFU of viable bacterium or spores/in$^2$ of external surface of baked good. Following drying, the baked good is ready for immediate use, storage in a sterile package, or for freezing.

The active ingredients (i.e., live bacteria or extracellular components), comprise about 0.01% to about 50% by weight of the final composition, preferably 0.01% to 10% by weight of the final baked good. Preferably, the isolated *Bacillus coagulans* comprise between about 0.01% and about 0.1% by weight of the baked good.

In one aspect, the amount of bacteria is about $10^4$ to $10^{14}$ colony forming units (CFU) of bacteria per gram of baked good (i.e., vegetative cells and/or bacterial spores), preferably $10^5$ to CFU/g. More preferably, the concentrations are $10^8$ to $10^{13}$ CFU/g; $10^9$ to $10^{12}$ CFU/g; or $10^{10}$ to $10^{11}$ CFU/g. In one aspect, the amount of bacteria is about $1 \times 10^6$ CFU per baked good. Alternatively, the amount of bacteria is about $2 \times 10^{10}$ CFU/5 lbs of batter. The actual amount in a composition will vary depending upon the amounts of composition to be dispersed into the baked good and upon routes of dispersal.

In one aspect, the isolated *Bacillus coagulans* comprise between about 0.01% to about 10%; 0.01% to about 1%; or about 0.05% to about 0.1% by weight of the baked good. Optionally, the isolated *Bacillus coagulans* comprise about 1 mg to about 10 g; about 10 mg to about 1 g; or about 25 mg to about 75 mg by weight of the baked good.

In one aspect, the finished baked good is frozen and stored in a sterile package prior to consumption. The invention also provides for storing the baked good in a sterile package at room temperature prior to consumption. Alternatively, the baked goods are consumed immediately. In one aspect, the *Bacillus coagulans* spores survive storage (shelf-life), i.e., retain viability or the ability to germinate at physiological conditions (e.g., ingestion), from about 12 days to about 2 years; from about 1 month to about 18 months; from about 3 months to about 1 year; or from about 6 months to about 9 months. In one aspect, the *Bacillus coagulans* of the invention survives storage (shelf-life) in muffins for at least about 12 days. In another aspect, the *Bacillus coagulans* of the invention survives storage (shelf-life) in frozen pizza for at least about 2 years. In yet another aspect, the *Bacillus coagulans* of the invention survives storage (shelf-life) in food bars for at least about 6 to at least about 18 months.

Example 1

Preparation of *Bacillus coagulans* Cultures

*Bacillus coagulans* Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg $MnSO_4$, and 1,000 ml distilled water, adjusted to pH 7.0, using a standard airlift fermentation vessel at 30° C. The range of $MnSO_4$ acceptable for sporulation is 1 mg/1 to 1 g/l. The vegetative cells can actively reproduce up to 45° C., and the spores are stable up to 90° C. After fermentation, the *B. coagulans* bacterial cells or spores are collected using standard methods (e.g., filtration, centrifugation) and the collected cells and spores can be lyophilized, spray-dried, air-dried or frozen. As described herein, the supernatant from the cell culture is collected and used as an extracellular agent secreted by *B. coagulans*.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing *B. coagulans* Hammer spores at room temperature is about 10 years.

Example 2

Preparation of *Bacillus coagulans* Spores

A culture of dried *B. coagulans* spores was prepared as follows. Ten million spores were inoculated into a one liter culture containing 24 g potato dextrose broth, 10 g of enzymic-digest of poultry and fish tissue, 5 g of FOS and 10 g MnSO4. The culture was maintained for 72 hours under a high oxygen environment at 37° C. to produce culture having about 150 billion cells per gram of culture. Thereafter, the culture was filtered to remove culture medium liquid, and the bacterial pellet was resuspended in water and freeze-dried. The freeze-dried powder is then ground to a fine powder using standard good manufacturing practice (GMP).

Example 3

Baked Muffin with Micro-Encapsulated *Bacillus coagulans*

GBI-30, ATCC Designation Number PTA-6086, was microencapsulated (Maxx Performance; Chester, N.Y.) and added in dry powder form to blueberry bran muffin batter. The final concentration of *Bacillus coagulans* (both vegetative cells and spores) in the batter was about 20 billion ($2 \times 10^{10}$) CFU/5 lbs of batter (yield about 20 muffins). The final concentration of *Bacillus coagulans* (both vegetative cells and spores) in each muffin was about 1 billion ($1 \times 10^6$) CFU/muffin. The isolated *Bacillus coagulans* comprised about 50 mg by weight per four ounce muffin. The muffins were cooked at 350° F. for 15 minutes. Subsequently, the muffins were frozen and stored at 0° F. for 14 days. The muffins were then thawed, crushed, and the number of viable bacteria was determined. Unexpectedly, approximately 41% of the bacteria in the muffin were viable after the above-mentioned cooking and freezing cycle.

What is claimed is:

1. A chemically leavened baked good comprising an edible starch and isolated *Bacillus coagulans* spores, wherein said isolated *Bacillus coagulans* spores comprise *Bacillus coagulans* Hammer spores, and wherein said spores in the baked good remain viable and germination-competent after baking.

2. The baked good of claim 1, wherein said isolated *Bacillus coagulans* spores comprise between 0.01% and 0.05% by weight of said baked good.

3. The chemically leavened baked good of claim 1, wherein said *Bacillus coagulans* Hammer spores comprise the spores of *Bacillus coagulans* Hammer strain Accession No. ATCC 31284.

4. The baked good of claim 1 wherein said *Bacillus coagulans* Hammer spores comprise the spores of GBI-20 strain (ATCC Designation Number PTA-6085).

5. The baked good of claim 1 wherein said *Bacillus coagulans* Hammer spores comprise the spores of GBI-40 strain (ATCC Designation Number PTA-6087).

6. The baked good of claim 1, further comprising a vegetative cell of *Bacillus coagulans* Hammer.

7. The baked good of claim 1, further comprising a fat selected from the group consisting of oil, butter, shortening, artificial lipid, synthetic fat, and a fat substitute.

8. The baked good of claim 1, further comprising a sugar, sugar substitute, or artificial sweetener.

9. A method of making a chemically leavened baked good, the method comprising:
   providing a flour containing base mix and a liquid portion of water;
   mixing said flour containing base mix and said water to form a batter or dough;
   applying an isolated *Bacillus coagulans* Hammer to a surface of said batter or dough; and
   heat processing said batter or dough to produce said chemically leavened baked good,
   wherein said isolated *Bacillus coagulans* Hammer comprises spores, and wherein the spores are viable and germination-competent after heat processing.

10. The method of claim 9, wherein said isolated *Bacillus coagulans* Hammer is *Bacillus coagulans* Hammer strain Accession No. ATCC 31284.

11. The method of claim 9, wherein said isolated *Bacillus coagulans* Hammer is GBI-20 strain (ATCC Designation Number PTA-6085).

12. The method of claim 9, wherein said isolated *Bacillus coagulans* Hammer is GBI-40 strain (ATCC Designation Number PTA-6087).

13. The method of claim 9, wherein said isolated *Bacillus coagulans* Hammer further comprises a vegetative cell.

14. The method of claim 9, wherein said isolated *Bacillus coagulans* Hammer comprise between 0.01% and 0.05% by weight of said chemically leavened baked good.

15. A method of making a chemically leavened baked good, the method comprising:
   providing a flour containing base mix and a liquid portion of water;
   mixing said flour containing base mix and said water to form a batter or dough;
   combining an isolated *Bacillus coagulans* Hammer with said batter or dough; and
   heat processing said batter or dough to produce said chemically leavened baked good,
   wherein said isolated *Bacillus coagulans* Hammer comprises spores, and wherein the spores are viable and germination-competent after heat processing.

16. The method of claim 15, wherein said isolated *Bacillus coagulans* Hammer is *Bacillus coagulans* Hammer strain Accession No. ATCC 31284.

17. The method of claim 15, wherein said isolated *Bacillus coagulans* Hammer is GBI-20 strain (ATCC Designation Number PTA-6085).

18. The method of claim 15, wherein said isolated *Bacillus coagulans* Hammer is GBI-40 strain (ATCC Designation Number PTA-6087).

19. The method of claim 15, wherein said isolated *Bacillus coagulans* Hammer further comprises a vegetative cell.

20. A composition comprising a dry mix for chemically leavened baked good comprising a flour and an isolated *Bacillus coagulans* Hammer spores, wherein the spores are viable and germination-competent after heat processing.

21. The composition according to claim 20, wherein the isolated *Bacillus coagulans* Hammer spores comprise spores of a *Bacillus coagulans* Hammer strain selected from the group consisting of GBI-20 strain (ATCC Designation Number PTA-6085), GBI-30 strain (ATCC Designation Number PTA-6086) and GBI-40 strain (ATCC Designation Number PTA-6087).

* * * * *